United States Patent [19]  [11] 4,330,536
Pissiotas et al. [45] May 18, 1982

[54] OXIME PHOSPHATES AND THEIR USE FOR COMBATING PESTS

[75] Inventors: Georg Pissiotas, Lörrach, Fed. Rep. of Germany; Ernst Beriger, Allschwil, Switzerland

[73] Assignee: Ciba-Geigy Corporation, Ardsley, N.Y.

[21] Appl. No.: 237,238

[22] Filed: Feb. 23, 1981

[30] Foreign Application Priority Data

Mar. 7, 1980 [CH] Switzerland ............. 1820/80
Sep. 17, 1980 [CH] Switzerland ............. 6972/80
Jan. 15, 1981 [CH] Switzerland ............. 243/81

[51] Int. Cl.³ .................. A01N 57/00; C07F 9/06
[52] U.S. Cl. ............................. 424/200; 546/24
[58] Field of Search ...................... 546/24; 424/200

[56] References Cited

U.S. PATENT DOCUMENTS 3,469,004  9/1969  Kaufman et al. ............. 424/202
3,968,222  7/1976  Drabek et al. ............... 424/200
4,132,784  1/1979  Malhotra ..................... 424/200

Primary Examiner—Ethel G. Love
Attorney, Agent, or Firm—Frederick H. Rabin

[57] ABSTRACT

Oxime phosphates of the formula

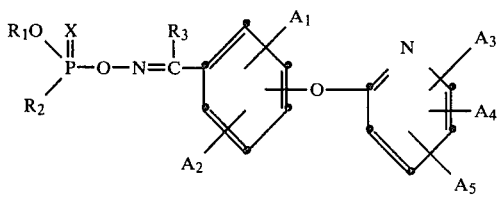

wherein
$R_1$ is $C_1$–$C_6$-alkyl,
$R_2$ is $C_1$–$C_7$-alkoxy or $C_1$–$C_6$-alkylthio,
$R_3$ is hydrogen, $C_1$–$C_6$-alkyl or cyano,
$A_1$, $A_2$, $A_3$ and $A_4$ are each hydrogen or halogen,
$A_5$ is hydrogen, halogen, trifluoromethyl or $C_1$–$C_6$-alkyl, and
X is oxygen or sulfur, a process for producing them, and their use for combating pests.

10 Claims, No Drawings

OXIME PHOSPHATES AND THEIR USE FOR COMBATING PESTS

The present invention relates to oxime phosphates, to processes for producing them, and to their use for combating pests.

The oxime phosphates have the formula I $$\underset{R_2}{\overset{R_1O}{\diagdown}}\underset{\parallel}{\overset{X}{P}}-O-N=C\underset{A_2}{\overset{R_3\quad A_1}{\diagdown}}\underset{A_5}{\overset{N\quad A_3}{\diagdown}} \quad (I)$$

wherein
$R_1$ is $C_1-C_6$-alkyl,
$R_2$ is $C_1-C_7$-alkoxy or $C_1-C_6$-alkylthio,
$R_3$ is hydrogen, $C_1-C_6$-alkyl or cyano,
$A_1$, $A_2$, $A_3$ and $A_4$ are each hydrogen or halogen,
$A_5$ is hydrogen, halogen, trifluoromethyl or $C_1-C_6$-alkyl, and
X is oxygen or sulfur.

Halogen in this case is fluorine, chlorine, bromine or iodine, particularly however chlorine or bromine.

The alkyl, alkoxy or alkylthio groups concerned can be straight-chain or branched-chain. Examples of such groups are, inter alia: methyl, methoxy, ethyl, ethoxy, n-propyl, n-propoxy, n-propylthio, isopropyl, n-, i-, sec- or tert-butyl, n-, i- or sec-butylthio, n-pentyl, or n-hexyl and isomers thereof.

Compounds of the formula I which are preferred on account of their action are those wherein
$R_1$ is methyl or ethyl,
$R_2$ is methoxy, ethoxy, n-propylthio, n-butylthio, iso-butylthio or sec-butylthio,
$R_3$ is hydrogen, methyl or cyano,
$A_1$, $A_2$, $A_3$ and $A_4$ are each hydrogen, chlorine, bromine or fluorine,
$A_5$ is hydrogen, chlorine, trifluoromethyl or methyl, and
X is oxygen or sulfur.

Particularly preferred compounds of the formula I are those wherein
$R_1$ is methyl or ethyl,
$R_2$ is methoxy, ethoxy, n-propylthio, n-butylthio iso-butylthio or sec-butylthio,
$R_3$ is hydrogen, methyl or cyano,
$A_1$ and $A_2$ are each hydrogen,
$A_3$ and $A_4$ are each hydrogen, chlorine, bromine or fluorine,
$A_5$ is hydrogen, chlorine, trifluoromethyl or ethyl, and
X is oxygen or sulfur.

More particularly preferred compounds of the formula I are those wherein
$R_1$ is ethyl,
$R_2$ is ethoxy or n-propylthio,
$R_3$ is hydrogen or methyl,
$A_1$, $A_2$ and $A_3$ are each hydrogen,
$A_4$ and $A_5$ are each chlorine, and
X is sulfur;
or wherein
$R_1$ is ethyl,
$R_2$ is ethoxy or n-propylthio,
$R_3$ is hydrogen or methyl,
$A_1$, $A_2$ and $A_3$ are each hydrogen,
$A_4$ and $A_5$ are each chlorine, and
X is oxygen.

The compounds of the formula I are produced by methods known per se, for example as follows:

(1) $\underset{R_2}{\overset{R_1O}{\diagdown}}\underset{\parallel}{\overset{X}{P}}-Hal + HO-N=C\underset{A_2}{\overset{R_3\quad A_1}{\diagdown}}\underset{A_5}{\overset{N\quad A_3}{\diagdown}} \xrightarrow{\text{acid-binding agent}} I$ (II)        (III)

(2) $\underset{R_2}{\overset{R_1O}{\diagdown}}\underset{\parallel}{\overset{X}{P}}-Hal + MO-N=C\underset{A_2}{\overset{R_3\quad A_1}{\diagdown}}\underset{A_5}{\overset{N\quad A_3}{\diagdown}} \longrightarrow I$ (II)        (IV)

(3) Production of compounds of the formula I wherein $R_2 = C_1-C_6-$alkylthio and X = oxygen:

$\underset{R_1O}{\overset{R_1O}{\diagdown}}\underset{\parallel}{\overset{S}{P}}-Hal + HON=C\underset{A_2}{\overset{R_3\quad A_1}{\diagdown}}\underset{R_5}{\overset{N\quad A_3}{\diagdown}} \xrightarrow{\text{acid-binding agent}} VII$ (V)        (VI)

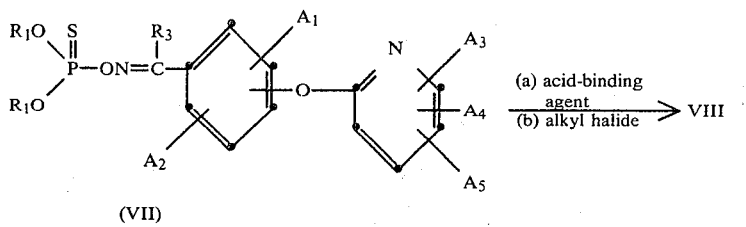

(VII)

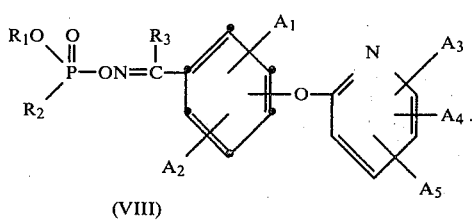

(VIII)

In the formulae II to VIII, the symbols $R_1$, $R_2$, $R_3$, $A_1$ to $A_5$ and X have the same meanings as for the formula I, "Hal" is a halogen atom, particularly chlorine or bromine, and M is an alkali metal atom or the ammonium radical.

Suitable acid-binding agents for the processes 1-3 are in particular: tertiary amines, such as trialkylamine and pyridine, also hydroxides, oxides, carbonates and bicarbonates of alkali metals and alkaline-earth metals, as well as alkali metal alcoholates, for example potassium tert-butylate and sodium methylate.

The processes 1 to 3 are performed at a reaction temperature of between $-10°$ and $120°$ C., usually between $20°$ and $80°$ C., under normal or elevated pressure and preferably in an inert solvent or diluent. Suitable solvents or diluents are for example: ethers and ethereal compounds, such as diethyl ether, dipropyl ether, dioxane, dimethoxyethane or tetrahydrofuran; amides, such as N,N-dialkylated carboxylic acid amides; aliphatic, aromatic as well as halogenated hydrocarbons, especially benzene, toluene, xylene, chloroform or chlorobenzene; nitriles, such as acetonitrile; dimethylsulfoxide, and ketones, such as acetone or methyl ethyl ketone.

The starting materials of the formulae II to VIII are known or they can be produced by known methods.

The compounds of the formula I are suitable for combating pests on animals and plants. Furthermore, these compounds have fungicidal and plant-growth-regulating properties.

The compounds of the formula I are particularly suitable for combating insects, for example of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera; and for combating mites and ticks of the order Acarina.

The compounds of the formula I are above all suitable for combating insects that damage plants, especially insects that damage plants by eating, in crops of ornamental plants and productive plants, in particular in cotton crops (for example against *Spodoptera littoralis* and *Heliothis virescens*), and in vegetable crops (for example against *Leptinotarsa decemlineata* and *Myzus persicae*). Active substances of the formula I have a very favourable action also against flies, such as *Musca domestica*, and against mosquito larvae, as well as against soil insects.

The compounds of the formula I can be used in a known manner either in an unmodified form or, together with auxiliaries customarily used in formulation practice, in the form of preparations, for example emulsion concentrates, suspension concentrates, directly sprayable solutions or dilutable solutions, diluted emulsions, wettable powders, soluble powders, dusts or granulates, and also superfine encapsulations in polymeric substances, and the like. The form of application, such as spraying, atomising, dusting, scattering or pouring, is governed entirely by the purpose of application. It is to be ensured however in this respect that the biological behaviour of the active substances of the formula I is not disadvantageously affected by the method of application, or by the type and amount of auxiliaries used for producing the preparation.

The preparations are produced in a known manner, for example by the intimate mixing and/or grinding of the active substances with extenders, such as with solvents or solid carriers, and optionally with surface-active substances (tensides). The solvents can be: aromatic hydrocarbons, preferably the fractions $C_8$ to $C_{12}$, i.e. xylene mixtures or substituted naphthalenes, aliphatic hydrocarbons, such as cyclohexane or paraffins, alcohols and glycols, as well as ethers and esters thereof, strongly polar solvents, such as dimethylsulfoxide or dimethylformamide, and also water. The solid carriers used, for example for dusts and dispersible powders, are mostly natural mineral fillers, such as calcite, talcum, kaolinite, montmorillonite or attapulgite. In order to improve the physical properties, it is also possible to add highly dispersed silicic acids or highly dispersed absorbent polymers. Suitable granulated adsorptive carriers are porous types, for example pumice, broken brick, sepiolite and bentonite; and suitable nonsorbent carriers are materials such as calcite or sand. In addition, a great number of pregranulated materials of inorganic or organic nature can be used, such as in particular dolomite, extending to pulverised plant residues.

Suitable surface-active substances are, depending on the polarity of the active substance of the formula I to be formulated, nonionic, cation-active and/or anion-active tensides having good emulsifying, dispersing and wetting properties; and by tensides are also meant tenside mixtures.

Suitable cation-active tensides are for example: quaternary ammonium compounds, such as cetyltrimethylammonium bromide. Suitable anion-active tensides are, inter alia: soaps, salts of aliphatic monoesters of sulfuric acid, such as sodium lauryl sulfate, salts of sulfonated aromatic compounds, for example sodium dodecylbenzene sulfonate, sodium-, calcium- and ammonium-lignin sulfonate, butylnaphthalene sulfonate or a mixture of the sodium salts of diisopropyl- and triisopropyl-naphthalene sulfonate. Suitable nonionogenic tensides are for example the condensation products of ethylene oxide with fatty alcohols, for example oleyl alcohol or cetyl alcohol, or with alkylphenols, such as octylphenol, nonylphenol or octylcresol. Other non-ionic agents are the partial esters derived from long-chain fatty acids and hexite anhydrides, and the condensation products of these partial esters with ethylene oxide, and lecithins.

The nonionogenic, anion-active and cation-active tensides commonly used in formulation practice are described in, inter alia, the following publication: "Mc Cutcheon's Detergents and Emulsifiers Annual," MC Publishing Corp., Ringewood, N.J., 1979.

The formulated compositions contain as a rule 0.1 to 99%, especially 0.1 to 95%, of active substance of the formula I, and 0 to 25% of a tenside, as well as 1 to 99.9% of a solid or liquid additive.

The compositions can also contain additives, such as stabilisers, defoaming agents, viscosity regulators, binders, adhesives as well as fertilisers or other active substances for producing special effects.

The active substances of the formula I can be formulated for example as follows (values are in percent by weight):

Dusts

The following substances are used to produce (a) a 5% dust and (b) a 2% dust:

(a)

5 parts of active substance, and
95 parts of talcum; and (b)

2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epoxidised vegetable oil,
0.25 part of cetyl polyglycol ether,
3.50 parts of polyethylene glycol, and
91 parts of kaolin (particle size 0.3–0.8 mm).

The active substance is mixed with epoxidised vegetable oil and the mixture is dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethylene-ethanol,
1.7 parts of Champagen chalk/hydroxyethyl cellulose mixture (1:1),
8.3 parts of sodium aluminium silicate,
16.5 parts of kieselguhr, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable Concentrates

The following substances are used to produce (a) a 10% emulsifiable concentrate, (b) a 25% emulsifiable concentrate and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulfonate calcium salt,
40 parts of dimethylformamide, and
43.2 parts of xylene;

(b)

25 parts of active substance,
2.5 parts of epoxidised vegetable oil,
10 parts of alkylarylsulfonate/fatty alcohol polyglycol ether mixture,
5 parts of dimethylformamide, and
57.5 parts of xylene; and (c)

50 parts of active substance, 4.2 parts of tributylphenol-polyglycol ether,
5.8 parts of calcium-dodecylbenzenesulfonate,
20 parts of cyclohexanone, and
20 parts of xylene.

Emulsions of the required concentration can be prepared from these concentrates by dilution with water.

Sprays

The following constituents are used to produce (a) a 5% spray and (b) a 95% spray:

(a)

5 parts of active substance,
1 part of epoxidised vegetable oil, and
94 parts of ligroin (boiling limits 160°–190° C.); and (b)

95 parts of active substance, and
5 parts of epoxidised vegetable oil.

The invention is further illustrated by the Examples which follow:

EXAMPLE 1

Production of the compound of the formula

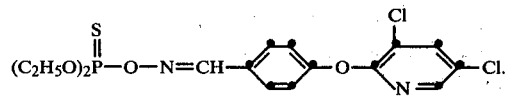

10 g of the sodium salt of 4-(2',4'-dichloropyridyl-1-oxy)-benzaldoxime are stirred together with 70 ml of dimethylformamide; 6 g of diethylthiochlorophosphate are then added dropwise at 20°–30° C., and the reaction mixture is stirred for a further 12 hours and is subsequently poured into ice water. The oil which precipitates is taken up in toluene, the toluene solution is washed with water, and the toluene is afterwards removed in vacuo at 50° C. bath temperature. The crude product is distilled off under high vacuum at 70° C. to yield 12 g of o,o-diethyl-o-(4-(3,5-dichloropyridyl-2-oxy)-benzaldoxime)-thiophosphorus having a melting point of 128°–123° C. The following compounds are produced in an analogous manner:

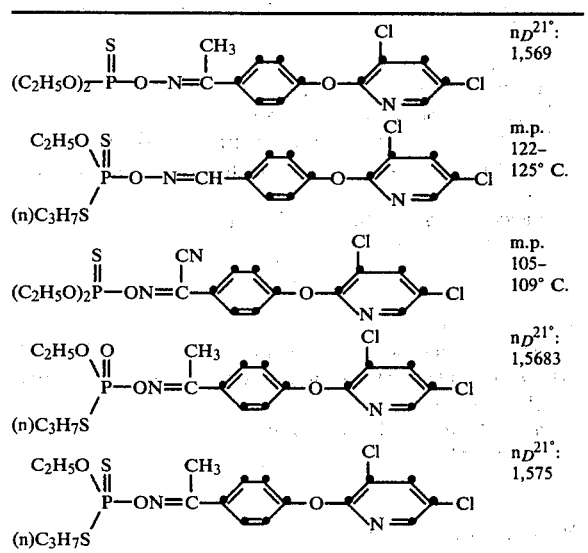

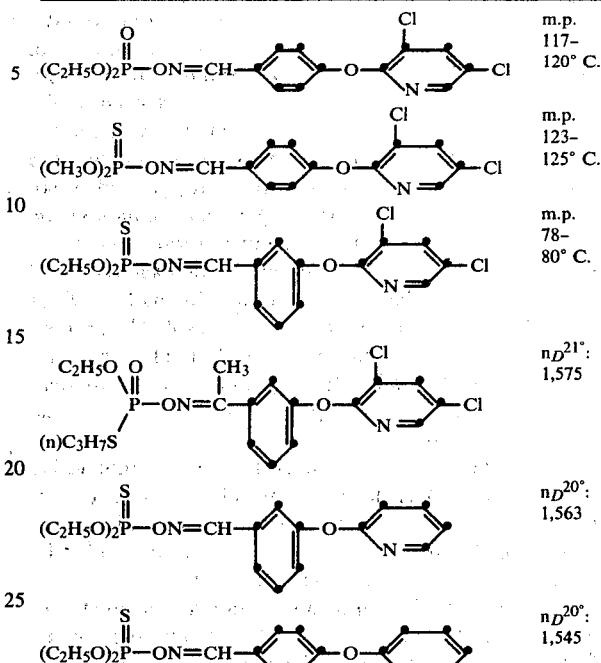

EXAMPLE 2

Insecticidal stomach-poison action: *Spodoptera littoralis*, *Dysdercus fasciatus* and *Heliothis virescens*

Cotton plants were sprayed with test solutions containing 50, 100, 200 and 400 ppm, respectively, of the compound to be tested. After the drying of the coating, larvae of the species *Spodoptera littoralis* ($L_3$ stage), *Dysdercus fasciatus* ($L_3$) and *Heliothis virescens* ($L_3$), respectively, were settled onto the plants. Two plants were used per test compound and per test species, and an evaluation of the attained mortality rate was made after 2, 4, 24 and 48 hours. The test was carried out at 24° C. with 60% relative humidity.

Within the concentration limits given above, the compounds according to the Production Example 1 were 100% effective against larvae of the species *Spodoptera littoralis*, *Dysdercus fasciatus* and *Heliothis virescens*.

EXAMPLE 3

Insecticidal contact action: *Myzus persicae*

Plants (*Vicia fabae*) grown in water were each infested before commencement of the test with about 200 individuals of the *Myzus persicae* species. The plants treated in this manner were sprayed dripping wet 3 days later with a solution containing 10 and 1 ppm, respectively, of the compound to be tested, from a distance of 30 cm. Two plants were used per test compound and per concentration, and an assessment of the mortality rate attained was made after a further 24 hours.

Within the concentration limits given above, compounds according to Example 1 were 100% effective against insects of the species *Myzus persicae*.

EXAMPLE 4

Insecticidal systemic action: *Aphis craccivora*

Rooted bean plants were transplanted to pots each containing 600 ccm of soil; and 50 ml of a test solution containing 25 ppm, 5 ppm and 1 ppm, respectively, of the compound to be tested was subsequently poured directly onto the soil. After 24 hours, aphids (*Aphis craccivora*) were settled onto the parts of plants above the soil, and a plastics cylinder was placed over each plant and drawn to by tying at the bottom in order to protect the aphids from any contact or gas action of the test substance. The evaluation of the mortality rate achieved was made 24 and 48 hours after commencement of the test. Two plants, each in a separate pot, were used per concentration level of test substance. The test was carried out at 25° C. with 70% relative humidity.

Within the concentration limits given above, compounds according to Example 1 had a 100% systemic action against insects of the species *Aphis craccivora*.

EXAMPLE 5

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 and 7 days, by examination under a binocular microscope, of the living larvae and of the dead larvae, adults and eggs, and the results were expressed as percentages. The treated plants were kept during the "holding time" in greenhouse compartments at 25° C.

EXAMPLE 6

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The test tubes were then sealed with a standardised cotton plug, and inverted so that the active-substance emulsion could be absorbed by the cotton wool. The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Within the concentration limits given above, compounds compounds according to Example 1 were effective in this test against adults and larvae of *Rhipicephalus bursa* and against sensitive and OP-resistant larvae, respectively, of *Boophilus microplus*.

EXAMPLE 7

Action against soil insects

One liter of compost soil was mixed with 64 mg of wettable powder containing 25% of active substance. Young zucchetti plants (*Cucumis pepo*) were potted with the treated soil in plastic pots (three plants per pot of 7 cm diameter). The pots immediately afterwards were infested in each case with 5 larvae of *Aulacophora femoralis*, Pachnoda and Chortophila, respectively, each test species being placed into a separate pot. An evaluation was made 4, 8, 16 and 32 days after introduction of the larvae. In the case of an 80–100% mortality on the first evaluation, a fresh infestation was carried out with 5 larvae of each species in the same soil sample again using 3 fresh zucchetti plants per pot. Where the action was less than 80%, the surviving larvae remained in the test soil until the following evaluation. When a substance effected a 100% mortality rate with an applied amount of 8 kg per hectare, a further assessment was made with 4 kg and 2 kg, respectively, of active substance per hectare.

Compounds according to Example 1 exhibited in the above test a 100% degree of effectiveness against larvae of *Aulacophora femoralis*, Pachnoda and Chlortophila.

| | Minimum concentration in ppm to effect 100% mortality of | | | | |
|---|---|---|---|---|---|
| | Spodoptera littoralis larvae | Aphid craccivora | Tetranychus urticae larvae | Rhipicephalus bursa larvae | X mg of AS per 1 liter of soil to effect 100% mortality of Pachnoda larvae |
| 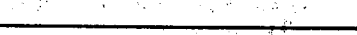 | 100 | .5 | 400 | 10 | 16 mg |
|  | 100 | 5 | 200 | 10 | 16 mg |
|  | 50 | 5 | 200 | 1 | — |
|  | 200 | 5 | 400 | 10 | — |

| | Minimum concentration in ppm to effect 100% mortality of | | | | |
|---|---|---|---|---|---|
| | Spodoptera littoralis larvae | Aphid cracivora | Tetranychus urticae larvae | Rhipicephalus bursa larvae | X mg of AS per 1 liter of soil to effect 100% mortality of Pachnoda larvae |
| $\underset{(n)C_3H_7S}{C_2H_5O}\overset{S}{\underset{\|}{\diagdown}}P-ON=\underset{CH_3}{C}-\text{phenyl-O-pyridyl(Cl,Cl)}$ | 200 | 20 | 400 | 10 | — |
| $(C_2H_5O)_2\overset{O}{\underset{\|}{P}}-ON=CH-\text{phenyl-O-pyridyl(Cl,Cl)}$ | 100 | 5 | 400 | 10 | 16 mg |
| $(CH_3O)_2\overset{S}{\underset{\|}{P}}-ON=CH-\text{phenyl-O-pyridyl(Cl,Cl)}$ | 200 | 5 | 400 | 10 | — |
| $(C_2H_5O)_2\overset{S}{\underset{\|}{P}}-ON=CH-\text{phenyl-O-pyridyl(Cl,Cl)}$ | 400 | 20 | 400 | 10 | — |
| $\underset{(n)C_3H_7S}{C_2H_5O}\overset{O}{\underset{\|}{\diagdown}}P-ON=\underset{CH_3}{C}-\text{phenyl-O-pyridyl(Cl,Cl)}$ | 100 | 5 | 400 | 10 | — |
| $(C_2H_5O)_2\overset{S}{\underset{\|}{P}}-ON=CH-\text{phenyl-O-pyridyl}$ | 100 | 20 | 200 | 1 | — |
| $(C_2H_5O)_2\overset{S}{\underset{\|}{P}}-ON=CH-\text{phenyl-O-pyridyl}$ | 200 | 20 | 400 | 10 | — |
| $\underset{(n)C_3H_7S}{C_2H_5O}\overset{O}{\underset{\|}{\diagdown}}P-O-\text{phenyl(CH(CH_3)_2)-SCH_3}$ | 800 | — | 800 | — | — | known from German Offenlegungsschrift No. 2,163,391

What is claimed is:

1. An oxime phosphate of the formula

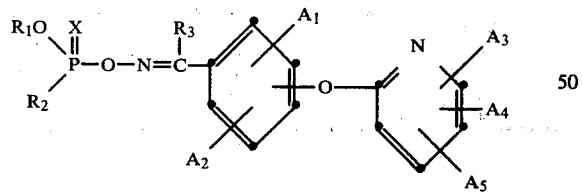

wherein
$R_1$ is $C_1$-$C_6$-alkyl,
$R_2$ is $C_1$-$C_7$-alkoxy or $C_1$-$C_6$-alkylthio,
$R_3$ is hydrogen, $C_1$-$C_6$-alkyl or cyano,
$A_1$, $A_2$, $A_3$ and $A_4$ are each hydrogen or halogen,
$A_5$ is hydrogen, halogen, trifluoromethyl or $C_1$-$C_6$-alkyl, and
X is oxygen or sulfur.

2. A compound according to claim 1, wherein
$R_1$ is methyl or ethyl,
$R_2$ is methoxy, ethoxy, n-propylthio, n-butylthio, iso-butylthio or sec-butylthio,
$R_3$ is hydrogen, methyl or cyano,
$A_1$, $A_2$, $A_3$ and $A_4$ are each hydrogen, chlorine, bromine or fluorine, and
$A_5$ is hydrogen, chlorine, trifluoromethyl or methyl.

3. A compound according to claim 2, wherein
$A_1$ and $A_2$ are each hydrogen, and
$A_3$ and $A_4$ are each hydrogen, chlorine, bromine or fluorine.

4. A compound according to claim 3, wherein
$R_1$ is ethyl,
$R_2$ is ethoxy or n-propylthio,
$R_3$ is hydrogen or methyl,
$A_3$ is hydrogen,
$A_4$ and $A_5$ are each chlorine, and
X is sulfur.

5. A compound according to claim 3, wherein
$R_1$ is ethyl,
$R_2$ is ethoxy or n-propylthio,
$R_3$ is hydrogen or methyl,
$A_3$ is hydrogen,
$A_4$ and $A_5$ are each chlorine, and
X is oxygen.

6. The compound according to claim 4 of the formula

7. The compound according to claim 4 of the formula

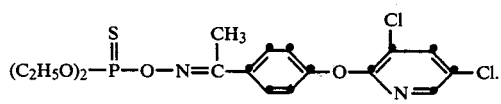

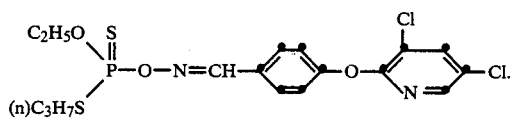

8. The compound according to claim 5 of the formula

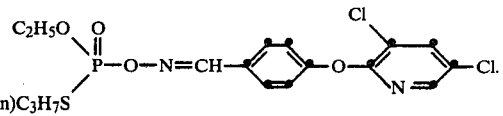

9. A insecticidal composition which comprises an insecticidally effective amount of a compound according to claim 1 as active ingredient, and suitable carriers and/or other additives.

10. A method of combating insects on animals and plants, which method comprises applying thereto an insecticidally effective amount of a compound according to claim 1.

* * * * *